US 6,568,307 B1

(12) United States Patent
Günther et al.

(10) Patent No.: US 6,568,307 B1
(45) Date of Patent: May 27, 2003

(54) MICROTOME HAVING A MOTORIZED FEED DRIVE SYSTEM

(75) Inventors: Bernd Günther, Neidenstein (DE); Siegbert Holtermüller, Heidelberg (DE); Peter Scheck, Rauenberg (DE); Andreas Laudat, Meckesheim (DE); Rolf Metzner, Dossenheim (DE); Roland Walter, Altlussheim (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 0 days.

(21) Appl. No.: 09/524,542

(22) Filed: Mar. 13, 2000

(30) Foreign Application Priority Data

Mar. 12, 1999 (DE) .......................... 199 11 173

(51) Int. Cl.⁷ ................................ G01N 1/06
(52) U.S. Cl. ........................ 83/367; 83/421; 83/915.5
(58) Field of Search .................. 83/915.5, 36, 733, 83/367, 421

(56) References Cited

U.S. PATENT DOCUMENTS

| 3,667,330 A | | 6/1972 | Kobernick ................... 83/98 |
| 4,377,958 A | * | 3/1983 | Leighton ................. 83/410.7 |
| 4,691,151 A | | 9/1987 | Behme et al. .............. 318/571 |
| 5,282,404 A | * | 2/1994 | Leighton et al. .............. 83/13 |
| 5,535,654 A | | 7/1996 | Niesporek et al. ............ 83/364 |
| 5,609,083 A | * | 3/1997 | Persson ......................... 83/14 |
| 5,761,977 A | | 6/1998 | Jakobi et al. .................. 83/13 |
| 5,782,572 A | | 7/1998 | Thiem ......................... 403/90 |

FOREIGN PATENT DOCUMENTS

| DE | 35 00 596 | 7/1986 |
| DE | 196 04 001 | 8/1997 |
| DE | 42 05 256 | 3/1998 |
| EP | 0 762 104 | 3/1997 |
| WO | WO 91/15746 | 10/1991 |
| WO | WO 98/04898 | 2/1998 |

OTHER PUBLICATIONS

U.S. patent application Ser. No. 09/700,161, Guenther et al., filed Feb. 1, 2001.

* cited by examiner

Primary Examiner—Kenneth E. Peterson
(74) Attorney, Agent, or Firm—Foley & Lardner

(57) ABSTRACT

A microtome (1) having a motorized feed drive system (2) for generating a relative movement between an object (7) that is to be cut and a cutting knife (4). A control circuit (8) and a pressure-sensitive sensor (9) are provided for detecting a position between the cutting knife (4) and the object (7). The motorized feed drive system (2) is switched via the control circuit (8) when the sensor (9) responds. The sensor (9) is equipped with a sensor surface (14) that is at least exactly as large as the surface (16) of the object (7). The sensor surface (14) is arranged parallel to the cutting plane (17).

22 Claims, 2 Drawing Sheets

MICROTOME HAVING A MOTORIZED FEED DRIVE SYSTEM

BACKGROUND OF THE INVENTION

1. Field of the Invention

The present invention relates to a microtome having a motorized feed drive system for generating a relative movement between an object that is to be cut and a cutting knife. The drive system includes a control circuit and a pressure-sensitive sensor for detecting a defined position between the cutting knife and the object. The motorized feed drive system is switched via the control circuit when the sensor responds.

Modern microtomes are being equipped to an increasing extent with motorized drive means. The throughput of specimens to be sectioned is increased with a microtome of this kind. In automated microtomes, developments have also included equipping not only the cutting drive system for generating a movement between the object and the cutting knife, but also the system for feeding the object to the cutting knife (or the cutting knife to the object) with a motor. A microtome of this kind is depicted and described, for example, in WO 98 04 898 A1.

When an object is changed, for safety reasons the greatest possible spacing between the knife and the object is established. For that purpose, the feed drive system is moved into one end position. A relatively long distance must therefore be covered when an object to be sectioned first approaches the cutting knife. Since the distance between the object and the cutting knife is in most cases unknown, the displacement speed is kept correspondingly low.

For this reason it has become the practice, for example, to arrange in the displacement path sensors that switch off the feed drive system when they respond. A sensor of this kind that has a microswitch and a triggering tab joined thereto is known, for example, from DE 42 05 256 C2. Because there is little room in the feed area, an arrangement of this kind must be of very delicate configuration. This configuration has proven disadvantageous, however, since cut material is produced on the microtome during continuous cutting operation, and can clog the delicate arrangement. Reliable switching of the sensor during continuous operation therefore cannot be guaranteed.

2. Description of the Related Art

U.S. Pat. No. 4,691,151 discloses a control circuit for the feed drive system of a specimen mount on the cutting knife in which a distinction is made between coarse and fine modes. The feed movement for coarse operation is limited by a control device having a switch.

U.S. Pat. No. 3,667,330 also discloses a device for limiting the feed movement of the specimen holder. Here a switch is arranged on the microtome base.

The known limiting devices all suffer from the disadvantage that a mechanical switch that is triggered not by the specimen itself, but by the specimen holder or the moving component, is arranged in the movement path of the specimen holder or of the moving component. The size of the object being cut is not taken into consideration with these devices, however, so that in all these cases the switch must operate with a greater or lesser safety distance between the object and the cutting knife. With these devices, an exact approach can be made only manually. The known devices make no provision for correlating the cutting plane with the surface of the object.

SUMMARY OF THE INVENTION

It is therefore one object of the present invention to provide an improved microtome.

A further object of the invention is to provide a microtome having a motorized feed drive system that permits an unequivocal correlation between the position of the cutting plane and the object.

In accomplishing the foregoing objects, there has been provided in accordance with the present invention a microtome comprising a cutting knife and an object holder that are movable relative to one another; a motorized feed drive system for generating a relative movement between the object holder for holding an object that is to be cut and the cutting knife. The drive system includes a control circuit and a pressure-sensitive sensor for detecting a position between the cutting knife and the object, wherein the motorized feed drive system is activated by the control circuit in response to signals from the sensor, wherein the sensor comprises a sensor surface that is at least as large as the surface of the object, and the sensor surface is arranged parallel to a cutting plane defined by the cutting knife.

Further objects, features and advantages of the present invention will become apparent from the detailed description of preferred embodiments that follows, when considered with the accompanying figures of drawings.

DETAILED DESCRIPTION OF PREFERRED EMBODIMENTS

Figures 1, 3:
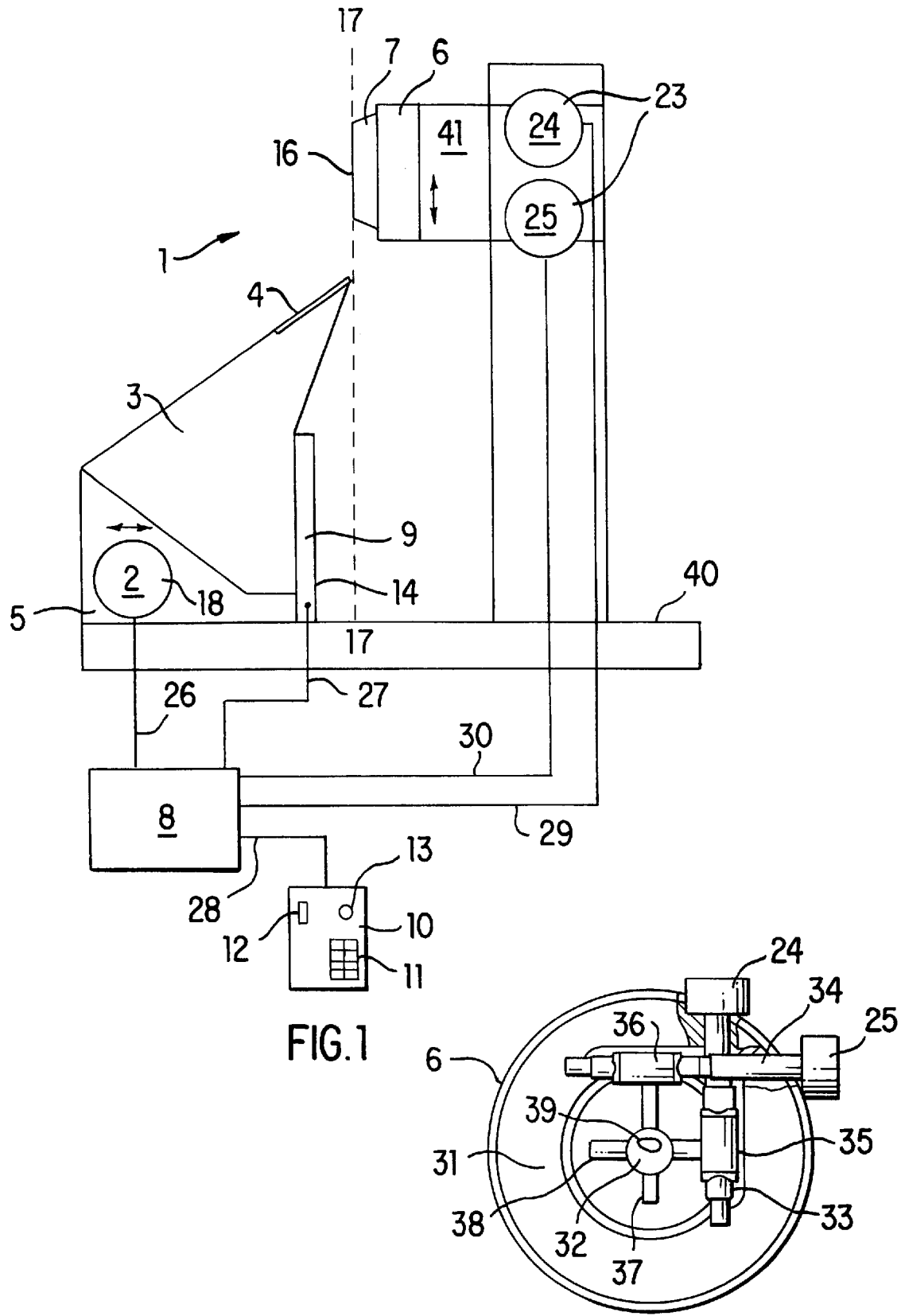
FIG. 1 is a schematic depiction of the microtome with a control device and an externally arranged control panel.
FIG. 3 is a detailed view of an object head that can be oriented in motorized fashion.

In the microtome according to the invention, in order to generate a relative movement between the object that is to be cut and the cutting knife, the motorized feed drive system is equipped with a control circuit and a pressure-sensitive sensor for detecting the position between the cutting knife and the object. When the sensor responds, the motorized feed drive system is switched by way of the control circuit, and this position of the feed drive system is memorized. The area of the sensor is preferably at least exactly as large as the surface of the object. The memorized position is used for automatically feeding the object to the cutting knife or vice versa. The sensor surface is, in this context, arranged parallel to the cutting plane.

The sensor responds by way of a contact between the sensor surface and the surface of the object. This has the advantage, as compared to conventional devices, that in this case the nature of the object and of its surface is directly taken into consideration.

The motorized feed device can have a stepper motor or a DC motor with an encoder. The motors and the encoder are electrically connected to the control circuit and can be controlled by it.

The position of the feed drive system and of its motors can be saved in the control circuit when the sensor responds. Since the position of the sensor with respect to the cutting plane is permanently defined, an unequivocal positional relationship with respect to the cutting plane can be created for each object surface of any shape. Using the saved position of the feed drive system and the unequivocal position of the cutting plane with respect to the position of the sensor, the object that is to be cut can be fed automatically to the cutting knife, or the knife can be fed automatically to the object.

The surface sensor can be, for example, a commercially available piezosensor or film touchpad. In a further embodiment of the invention, the sensor is configured as a position-sensitive surface sensor. The result of this is that the surface of the objects can easily be automatically aligned with the position of the cutting plane. This is particularly advantageous whenever a series of cuts are to be made on objects that have already been cut into or objects that have a smooth surface.

The position of the cutting plane, which may change, for example, as a result of a knife replacement, can also be ascertained. For this purpose, provision is made for an object first to be cut into under manual control. Then a contact is effected between the object surface and the sensor by way of the control circuit. This position of the feed drive system is saved in the control circuit and thus corresponds exactly to the position of the cutting plane. All subsequent objects, regardless of their size and surface structure, can use this position as a reference. This is possible only because the surface of the object triggers the sensor.

In a further embodiment of the invention, a control panel for manual input of modifiable parameters for controlling the feed drive system is provided, and is connected electrically to the control circuit. Of course the control circuit can also be arranged in the control panel. All the motor-adjustable settings, for example, the standard thickness of the specimens being cut, can then be preselected by way of the control panel.

In a preferred embodiment, the feed device is used together with a disk microtome. The object that is to be cut is arranged on the rotatably mounted component of the disk microtome.

The microtome can additionally have an object holder that can be oriented by means of one or more motors to be adjusted in two spatial directions. A manually orientable object holder for a microtome is known, for example, from DE 196 04 001 A1. By way of this object holder, the surface of the object can be aligned with the cutting plane.

In a particularly preferred embodiment of the present invention, provision is made for the drive motors to be electrically connected to the control circuit. For automatic orientation of an initially cut specimen, the object holder is brought in motorized fashion into a stop position. This is done, for example, by bringing both positioning motors into one of their end positions by way of the control circuit. Then a contact is effected, by way of the feed device, between the object surface and the sensor. By way of the control circuit, the object holder and the feed device are then activated in steps until no further signal is delivered by the sensor.

In a further preferred embodiment, provision is made of the drive system of the object holder initially to be controlled so that one corner of the object is directed maximally to the front. The motor-controlled contact between the object and the surface sensor then occurs. Upon contact, the orientation of the object is then changed by way of the positioning motors, and the object is once again brought closer. This procedure is performed until none of the changes in alignment results in any contact with the sensor.

Orientation of the object can, however, also be accomplished by using the control circuit to bring that both positioning motors initially into one of their end positions, so as then to effect a contact with the sensor. These and two further corner positions are moved to and are saved. By saving the path lengths while moving to the respective corners, the orientation of the object surface with respect to the cutting plane can be ascertained and set. Saving the path lengths while moving to the corners can be omitted if the surface sensor is configured as a position-sensitive surface sensor or a two-dimensional potentiometer pad.

The invention will be explained in more detail with reference to an exemplary embodiment with the aid of the schematic drawings. FIG. 1 shows a microtome 1 having a base bed 40 and a feed slide 5 arranged thereon for a knife holder 3 that carries a cutting knife 4. Feed slide 5 is movable on base bed 40 in the direction of the double arrow, and is driven by a motorized feed drive system 2 having a stepper motor 18. Stepper motor 18 is electrically connected via a control line 26 to a control circuit 8. Additionally arranged on feed slide 5 is a sensor 9 having a sensor surface 14. Sensor 9 is connected via a control line 27 to control circuit 8.

Provided on microtome 1 is an object head 41 that is movable in the direction of the double arrow, and has an object holder 6 arranged thereon for holding an object 7 that is to be cut. The surface 16 of object 7 is arranged in cutting plane 17. For cutting, object 7 is guided over cutting knife 4. Once a cut has been made, object holder 6 is moved back into its initial position. By way of motorized feed drive 2, feed slide 5 with cutting knife 4 is moved toward object 7 by an amount equivalent to the predefined cutting thickness. Then a further cut is performed.

It is self-evident that the movements just described can also be performed concurrently with one another. All that must be ensured in this context is that a collision with the cutting knife or the knife holder cannot occur during the return movement of the object.

Object head 41 can be oriented in two spatial directions by means of a motorized drive system 23. Provided for that purpose on the microtome are two stepping motors 23, 24 that are electrically connected to the control device via respective control lines 29 and 30.

A control panel 10 is also connected to control circuit 8 via a control line 28. The control panel has a keypad 11 for numerical inputs, a rotary controller 13 for continuously variable inputs, and a switch 12 for inputting specific switch positions and operating states.

It is of course also possible to provide a second control device, such as a footswitch, that not only delivers a start/stop pulse to the control circuit when actuated, but also allows other adjustable parameters for the motorized control of the microtome to be influenced by way of the control circuit. For example, a specific position can be moved to or a specific speed can be set if the footswitch is actuated at a specific frequency or for a specific period.

To ascertain the distance between cutting knife 4 or cutting plane 17 and sensor 9, an object is first cut into under manual control. This is necessary whenever, for example, a knife replacement or a change in the cutting angle has been performed, and the position of cutting plane 17 has changed. To ascertain and save the position of the cutting plane, motorized feed drive system 2 drives the feed slide 5 toward object surface 16 by operation of the switching means of control panel 10. Once a contact has been effected between the knife edge and object surface 16, the position of feed slide 5 is stored in control circuit 8. Object holder 6 is then positioned in front of sensor 9, and a contact between object surface 16 and sensor surface 14 is effected by way of feed slide 5. This position of motorized feed drive system 2 is also saved in control circuit 8. From the difference between these two values, the exact distance between cutting plane 17 and sensor surface 14 can be calculated. Since sensor surface 14 is selected to be larger than the surface of object 7, the highest point on object surface 16 is always taken into account, even with very irregular surfaces. The thickness and surface structure of object 7 that is to be cut are therefore entirely immaterial. Once the distance between sensor 9 and cutting plane 17 has been calculated, all objects 7 that are to be cut can be positioned automatically in cutting plane 17.

Automatic positioning of object 7 in cutting plane 17 is performed after object 7 has been replaced. For that purpose, first of all a contact is effected between object 7 and sensor 9 by way of motorized feed drive system 2. In control circuit 8, this position is added to the calculated difference between cutting plane 17 and sensor surface 14. Feed slide 5 is automatically moved into this recalculated position. It has proven to be advantageous if the object is not fed into the cutting plane at the maximum feed speed, but rather is decelerated immediately before the calculated position is reached, so that the feed drive system can then have applied to it the cutting thickness values predefined via control panel 10.

Previously cut specimens 7, or specimens with a smooth surface, can be automatically oriented with respect to cutting plane 17. This is done by the fact that object holder 6 is first brought into a stop position by way of stepper motors 24 and 25. Then a contact is effected between object surface 16 and sensor 9 by way of motorized feed drive system 2. Stepper motors 24, 25 and motorized feed drive system 2 are then activated in steps by control circuit 8 until no further signal is delivered by sensor 9.

Orientation of object surface 16 can also be accomplished, however, by the fact that both stepper motors 24 and 25 are first brought by control circuit 8 into one of their end positions, and a contact with sensor 9 is then effected. These and two further corner positions of object surface 16 are moved to and saved. By simultaneously acquiring the distances traveled while moving to the respective corner positions, the orientation of object surface 16 with respect to cutting plane 17 can be calculated and set.

Figure 2:
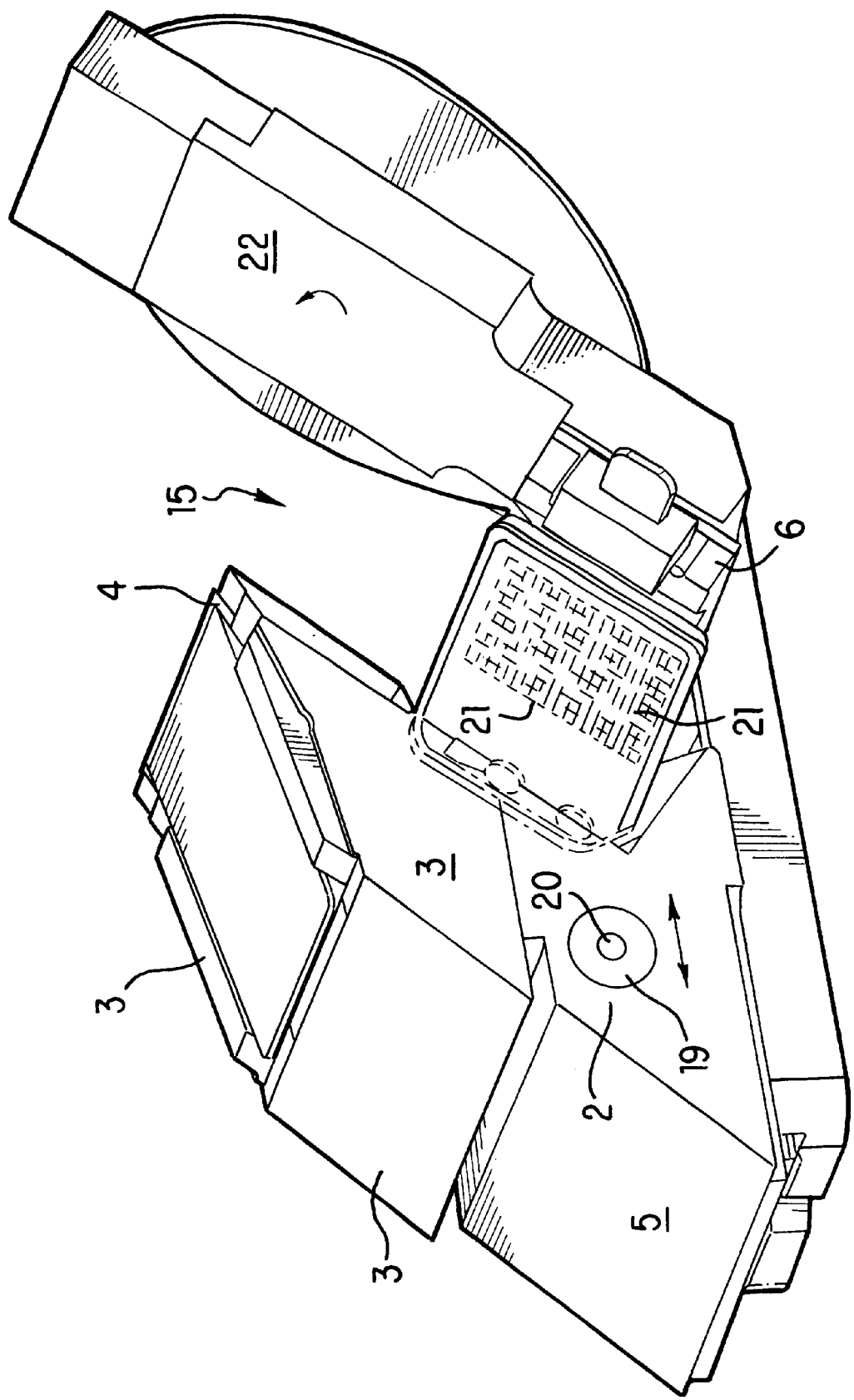
FIG. 2 is a perspective view of a disk microtome with a surface sensor.

Saving the path lengths when moving to the corners can be dispensed with if sensor 9 is configured as a position-sensitive surface sensor or two-dimensional potentiometer pad, as depicted in FIG. 2.

FIG. 2 shows a schematic depiction of a disk microtome 15 having motorized feed drive system 2, which in this case has a DC motor 19 and an associated encoder 20. The electrical connections to the control circuit are not depicted in this Figure.

Feed slide 5, to which a position-sensitive surface sensor 21 is attached, is movable by way of this motorized drive system. Object holder 6 is arranged on a rotatably mounted component 22 of disk microtome 15. The drive motor for rotatably mounted component 22, which can also be configured as a stepper motor, is not depicted here. Object holder 6 can be positioned, by way of rotationally movable component 22, in front of surface sensor 21 or in front of cutting knife 4. Positioning and orientation of the specimen that is to be cut are performed analogously to the exemplary embodiment of FIG. 1, with the difference that rotationally movable component 22 is moved only in one direction, and there is thus no risk of collision between knife 4 and the object when moving to the initial position.

FIG. 3 shows object head 41 that can be oriented by means of motors. A ball joint 31 and a ball 32 carry object holder 6. Object head 41 has two threaded spindles 33 and 34, arranged perpendicular to one another, each of which has associated with it one of the two stepper motors 24 and 25. Threaded spindles 33 and 34 are mounted rotatably in ball joint 31, and a nut 35 and 36 run respectively on the two spindles 33 and 34. Pins 37 and 38 are respectively shaped onto nuts 35 and 36.

A rotary movement of spindles 33 and 34 is transferred to nuts 37, 38 which then, together with pins 37, 38, move along the respective spindles 33, 34. The longitudinal movement of pin 37 is transferred via an oblong hole 39 to ball 32. This movement results in a lateral pivoting movement of object head 41 in the X direction.

Analogously, rotation of spindle 33 causes pin 38 to move in an oblong hole (not depicted), so that in this case object head 41 executes a pitching movement in the Y direction.

With the device described, it is possible to align object head 41 of a microtome in the X and/or Y direction by way of a motor-controlled drive unit.

The invention is not limited to a specific type of microtome illustrated, but can of course be used in a rotary microtome, a disk microtome, or a sliding microtome.

The disclosure of German Patent Application No. 199 11 173.1, filed Mar. 12, 1999, is hereby incorporated by reference in its entirety.

It will be readily apparent that many other embodiments of the present invention can be constructed in accordance with the teachings contained herein. It is intended that all such embodiments are encompassed by the appended claims.

We claim:

1. A microtome, comprising: a cutting knife and an object holder that are movable in a first direction relative to one another, wherein the cutting knife defines a cutting plane; a motorized feed drive system for generating a relative movement in the first direction between the cutting knife and the object holder, wherein the object holder is adapted for holding an object which is to be cut and which has a frontal surface facing in the first direction; and a cutting drive system for generating relative movement between the object holder and the cutting knife in the cutting plane, the feed drive system including a control circuit and a pressure-sensitive sensor for determining a relative position between the cutting knife and the object, wherein the sensor comprises a generally planar sensor surface that is at least as large as the frontal surface of the object, and the sensor surface is fixed in the first direction with respect to the cutting plane and is in an orientation that is parallel to the cutting plane, wherein the feed drive system and the cutting drive system are configured to selectively pre-position the object in front of said sensor and to provide relative movement between the object holder and said sensor until a leading edge of said object contacts said sensor, whereby said sensor generates a signal to said control circuit for determining said relative position, and wherein for final positioning of the object in preparation for cutting the object the motorized feed drive system is activated by the control circuit in response to said relative position determined based upon said signal from the sensor.

2. A microtome as defined in claim 1, wherein the pressure-sensitive sensor comprises a sensor that generates a signal in response to initial contact between the sensor surface and any surface of the object.

3. A microtome as defined in claim 1, further comprising a motorized device, operatively connected to the control circuit, for orienting the object holder relative to the cutting plane in response to signals received from the sensor.

4. A microtome as defined in claim 3, wherein the motorized device comprises two motors for orienting the object holder in two dimensions relative to the cutting plane.

5. A microtome as defined in claim 4, wherein the motorized device comprises a control system for automatically orienting the object holder in an orientation that aligns the frontal surface of the object with the cutting plane.

6. A microtome as defined in claim 5, wherein the control system includes an operating program that multiply orients the object holder, that for each orientation moves the object holder in the first direction by way of the motorized feed drive system until first contact is made between the object and the sensor and that measures the respective distances moved in each instance, and that selects an orientation based on said measured distances.

7. A microtome as defined in claim 5, wherein the sensor comprises a position-sensitive sensor that determines the position on the sensor surface at which contact with the object is first made, and the control system includes an operating program that multiply orients the object holder, that for each orientation moves the object holder in the first direction by way of the motorized feed drive system until first contact is made between the object and the sensor and that selects an orientation based on the positions of first contact determined.

8. A microtome as defined in claim 1, wherein the motorized feed drive system comprises a stepper motor electrically connected to the control circuit.

9. A microtome as defined in claim 1, wherein the motorized feed drive system comprises a DC motor and an encoder, and the DC motor and the encoder are electrically connected to the control circuit.

10. A microtome as defined in claim 1, wherein the control circuit includes a memory for saving a position of the feed drive system when the sensor responds.

11. A microtome as defined in claim 1, wherein the sensor comprises a piezosensor or film touchpad.

12. A microtome as defined in claim 1, wherein the sensor comprises a position-sensitive surface sensor that determines the position on the sensor surface at which contact with the object is first made.

13. A microtome as defined in claim 12, wherein the position-sensitive surface sensor comprises a two-dimensional potentiometer pad.

14. A microtome as defined in claim 1, wherein the control circuit is connected to a control panel that permits manual input of modifiable parameters for controlling the feed drive system.

15. A microtome as defined in claim 1, wherein the control circuit includes a system for adjusting the standard thickness of the objects that are to be cut.

16. A microtome as defined in claim 1, wherein the microtome comprises a disk microtome, and the object that is to be cut is arranged on a rotatably mounted component of the disk microtome.

17. A microtome as defined in claim 1, wherein the sensor is positioned in a plane that is displaced from said cutting plane in the direction of the cutting knife.

18. A microtome that is capable of automatically aligning the frontal surface of an object to be cut with the cutting plane of the microtome, comprising: a cutting knife and an object holder that are movable in a first direction relative to one another, wherein the cutting knife defines a cutting plane; a motorized feed drive system for generating a relative movement in the first direction between the cutting knife and the object holder for holding an object, wherein the object holder is adapted for holding an object which is to be cut and which has a frontal surface facing in the first direction; a cutting drive system for generating relative movement between the object holder and the cutting knife in the cutting plane, the feed drive system including a control circuit and a pressure-sensitive sensor for determining a relative position between the cutting knife and the object, wherein the sensor comprises a generally planar sensor surface that is at least as large as the frontal surface of the object, and the sensor surface is fixed in the first direction with respect to the cutting plane and is in an orientation that is parallel to the cutting plane, wherein the feed drive system and the cutting drive system are configured to selectively pre-position the object in front of said sensor and to provide relative movement between the object holder and said sensor until a leading edge of said object contacts said sensor, whereby said sensor generates a signal to said control circuit; and a motorized device, operatively connected to the control circuit, for adjusting an orientation angle of the object holder relative to the cutting plane in response to signals received from the sensor to automatically align the frontal surface of an object to be cut with the cutting plane of the microtome.

19. A microtome as defined in claim 18, wherein the motorized device comprises two motors for orienting the object holder in two dimensions relative to the cutting plane.

20. A microtome as defined in claim 19, wherein the motorized device comprises a control system for automatically orienting the object holder in an orientation that aligns the frontal surface of the object with the cutting plane.

21. A microtome as defined in claim 20, wherein the control system includes an operating program that multiply orients the object holder, that for each orientation moves the object holder in the first direction by way of the motorized feed drive system until first contact is made between the object and the sensor and that measures the respective distances moved in each instance, and that selects an orientation based on said measured distances.

22. A microtome as defined in claim 20, wherein the sensor comprises a position-sensitive sensor that determines the position on the sensor surface at which contact with the object is first made, and the control system includes an operating program that multiply orients the object holder, that for each orientation moves the object holder in the first direction by way of the motorized feed drive system until first contact is made between the object and the sensor and that selects an orientation based on the positions of first contact determined.

* * * * *